(12) United States Patent
Nakao et al.

(10) Patent No.: US 10,709,672 B2
(45) Date of Patent: Jul. 14, 2020

(54) POLYPHENOL-CONTAINING SOLID COMPOSITION (71) Applicant: SAN-EI GEN F.F.I., INC., Osaka (JP)

(72) Inventors: Tomohiro Nakao, Osaka (JP); Mikihiko Nakamura, Osaka (JP); Masayuki Nishino, Osaka (JP)

(73) Assignee: SAN-EI GEN F.F.I., INC., Osaka (JP)

( * ) Notice: Subject to any disclaimer, the term of this patent is extended or adjusted under 35 U.S.C. 154(b) by 78 days.

(21) Appl. No.: 15/767,044

(22) PCT Filed: Oct. 7, 2016

(86) PCT No.: PCT/JP2016/080036
§ 371 (c)(1),
(2) Date: Apr. 9, 2018

(87) PCT Pub. No.: WO2017/061627
PCT Pub. Date: Apr. 13, 2017

(65) Prior Publication Data
US 2018/0289635 A1 Oct. 11, 2018

(30) Foreign Application Priority Data
Oct. 9, 2015 (JP) .................................. 2015-201582

(51) Int. Cl.
| | | |
|---|---|---|
| A61K 31/05 | (2006.01) | |
| A61K 8/39 | (2006.01) | |
| A61K 8/86 | (2006.01) | |
| A61K 31/12 | (2006.01) | |
| A61K 47/14 | (2017.01) | |
| A61K 47/24 | (2006.01) | |
| A61K 47/26 | (2006.01) | |
| A61K 47/32 | (2006.01) | |
| A61K 47/34 | (2017.01) | |
| A61K 47/38 | (2006.01) | |
| A23L 5/00 | (2016.01) | |
| A23L 27/20 | (2016.01) | |
| A61K 31/366 | (2006.01) | |
| A61K 8/34 | (2006.01) | |
| C11B 9/00 | (2006.01) | |
| A61K 8/81 | (2006.01) | |
| A61K 9/14 | (2006.01) | |
| A61K 9/16 | (2006.01) | |
| A61Q 19/00 | (2006.01) | |
| A61K 8/73 | (2006.01) | |
| A61K 9/00 | (2006.01) | |

(52) U.S. Cl.
CPC ............... *A61K 31/05* (2013.01); *A23L 5/00* (2016.08); *A23L 27/20* (2016.08); *A23L 27/203* (2016.08); *A61K 8/342* (2013.01); *A61K 8/39* (2013.01); *A61K 8/731* (2013.01); *A61K 8/8176* (2013.01); *A61K 8/86* (2013.01); *A61K 9/0053* (2013.01); *A61K 9/146* (2013.01); *A61K 9/1682* (2013.01); *A61K 31/12* (2013.01); *A61K 31/366* (2013.01); *A61K 47/14* (2013.01); *A61K 47/24* (2013.01); *A61K 47/26* (2013.01); *A61K 47/32* (2013.01); *A61K 47/34* (2013.01); *A61K 47/38* (2013.01); *A61Q 19/00* (2013.01); *C11B 9/003* (2013.01); *C11B 9/0049* (2013.01); *A61K 2800/92* (2013.01)

(58) Field of Classification Search
CPC .......... A61K 31/05; A61K 8/342; A61K 8/39; A61K 8/731; A61K 8/8176; A61K 8/86; A61K 9/0053; A61K 9/146; A61K 9/1682; A61K 31/12; A61K 31/366; A61K 47/14; A61K 47/24; A61K 47/26; A61K 47/32; A61K 47/34; A61K 47/38
USPC ......................................................... 514/457
See application file for complete search history.

(56) References Cited

U.S. PATENT DOCUMENTS

| 6,790,903 B1 | 9/2004 | Majalo et al. |
| 2011/0201680 A1 | 8/2011 | Xu et al. |
| 2013/0303628 A1* | 11/2013 | Breitenbach ........... A61K 9/146 514/679 |

FOREIGN PATENT DOCUMENTS

| CN | 101095670 A | 1/2008 | |
| JP | H04-182434 A | 6/1992 | |
| JP | 2002-532589 A | 10/2002 | |
| JP | 2010-512384 A | 4/2010 | |
| JP | 2012-188450 A | 10/2012 | |
| JP | 2014-503470 A | 2/2014 | |
| KR | 2012-0077004 A | 7/2012 | |
| WO | WO-0033817 A1 * | 6/2000 | ............ A61K 9/146 |
| WO | 2008072954 A2 | 6/2008 | |
| WO | 2012049253 A1 | 4/2012 | |

OTHER PUBLICATIONS

Codex Alimentatius Commission (Codex committee on food additives and contaminants, thirty-third session, The Hague, The Netherlands Mar. 12-16, 2001) (Year: 2001).*

(Continued)

*Primary Examiner* — Yevgeny Valenrod
(74) *Attorney, Agent, or Firm* — Hamre, Schumann, Mueller & Larson, P.C.

(57) ABSTRACT

An object of the present invention is to provide a polyphenol-containing solid composition that enables efficient ingestion of a polyphenol. This object can be achieved by a solid composition containing (1) an amorphous poorly water-soluble polyphenol, (2) a hydrophilic polymer, and (3) at least one nonionic surfactant selected from the group consisting of polyglycerol fatty acid esters, sucrose fatty acid esters, and lecithins.

10 Claims, 4 Drawing Sheets (56) References Cited

OTHER PUBLICATIONS

JP2996716B2 machine translation (Year: 1990).*
Yadev et al., "Novel formulation of solid lipid microparticles of curcumin for anti-angiogenic and anti-inflammatory activity for optimization of therapy of inflammatory bowel disease", Journal of Pharmacy and Pharmacology, 2009, vol. 61, No. 3, pp. 311-321.
International Search Report and Written Opinion, International Patent Application No. PCT/JP2016/080036, dated Dec. 20, 2016, with English translation of Search Report (12 pages).
Extended European Search Report issued for European patent application No. 16853778.5, dated Jun. 3, 2019, 8 pages.

* cited by examiner

POLYPHENOL-CONTAINING SOLID COMPOSITION

TECHNICAL FIELD

The present invention relates to a polyphenol-containing solid composition and the like.

BACKGROUND ART

Polyphenols, such as curcumine, are considered to have physiological effects, such as action suppressing cholesterol level increases action suppressing blood pressure increases, action against allergies, and action reducing body fat. To expect such physiological effects, ingestion of large amounts of polyphenol is necessary.

Polyphenols are components contained in, for example, edible plants. Although polyphenols can be ingested, for example, in usual meals, ingesting polyphenols in the form of polyphenol-containing tablets or like solid compositions is convenient and efficient.

However, most polyphenols are poorly soluble in water. Therefore, even if a polyphenol-containing solid composition is ingested, polyphenols are dissolved and absorbed into the body fluid at slow rates.

To solve this problem, for example, Patent Literature (PTL) 1 suggests an oral composition comprising a curcuminoid and an essential oil of turmeric.

However, from the viewpoint of efficient ingestion of polyphenols, development of a new technique has been desired.

CITATION LIST

Patent Literature

PTL 1: JP2012-188450A

SUMMARY OF INVENTION

Technical Problem

The object of the present invention is to provide a polyphenol-containing solid composition that enables efficient ingestion of a polyphenol.

Solution to Problem

The present inventors carried out extensive search to solve the above problem by providing a polyphenol-containing solid composition with an enhanced ability to dissolve a polyphenol into the intestinal fluid. As a result, the inventors found that the above problem can be solved by a solid composition comprising (1) an amorphous poorly water-soluble polyphenol, (2) a hydrophilic polymer, and (3) at least one nonionic surfactant selected from the group consisting of polyglycerol fatty acid esters, sucrose fatty acid esters, and lecithins. The present invention has been accomplished based on this finding.

The present invention includes the following embodiments.

Item 1.
A solid composition comprising (1) an amorphous poorly water-soluble polyphenol, (2) a hydrophilic polymer, and (3) at least one nonionic surfactant selected from the group consisting of polyglycerol fatty acid esters, sucrose fatty acid esters, and lecithins.

Item 2.
The solid composition according to item 1, wherein the amorphous poorly water-soluble polyphenol is at least one member selected from the group consisting of curcumine, silymarin, and luteolin.

Item 3.
The solid composition according to Item 1 or 2, wherein the hydrophilic polymer is at least one member selected from the group consisting of polyvinylpyrrolidone, hydroxypropyl cellulose, and hydroxypropyl methylcellulose.

Item 4.
The solid composition according to any one of Items 1 to 3, wherein the nonionic surfactant is a polyglycerol fatty acid ester.

Item 5.
The solid composition according to any one of Items 1 to 4, which is an oral preparation.

Item 6.
A method for producing the solid composition according to any one of Items 1 to 5, comprising (1) a crystalline polyphenol, (2) a hydrophilic polymer, and (3) at least one nonionic surfactant selected from the group consisting of polyglycerol fatty acid esters, sucrose fatty acid esters, and lecithins.

Advantageous Effects of Invention

When orally administered or ingested, the solid composition of the present invention allows a polyphenol to dissolve at a high rate into the body fluid (preferably the intestinal fluid) for a prolonged period of time to thereby enable efficient ingestion of the polyphenol.

More specifically, the present invention can provide a polyphenol-containing solid composition that enables efficient ingestion of a polyphenol.

BRIEF DESCRIPTION OF THE DRAWINGS

FIG. 1-1 is a graph showing changes in dissolution of curcumine into simulated intestinal fluid over time from the curcumine-containing preparation obtained in Example 1, in comparison with those from a solid composition not containing a nonionic surfactant (Comparative Example 1), a solubilized preparation (Comparative Example 2), and a solid composition prepared without heating (Comparative Example 3).

FIG. 1-2 is a graph showing changes in dissolution of silymarin into simulated intestinal fluid over time from the silymarin-containing preparation obtained in Example 10, in comparison with those from a solid composition not containing a nonionic surfactant (Comparative Example 8), a solubilized preparation (Comparative Example 9), and a solid composition prepared without heating (Comparative Example 10).

FIG. 1-3 is a graph showing changes in dissolution of luteolin into simulated intestinal fluid over time from the luteolin-containing preparation obtained in Example 11, in comparison with those from a solid composition not containing a nonionic surfactant (Comparative Example 10) and a solubilized preparation (Comparative Example 11).

DESCRIPTION OF EMBODIMENTS

Term

The symbols and abbreviations used in this specification can be assumed to have their ordinary meanings used in the technical field to which the present invention pertains, as understood from the context of the specification, unless otherwise specified.

In the specification, the term "containing" is used to include the phrase "consisting essentially of" and the term "comprising."

The step, treatment, or operation disclosed in the specification can be performed at room temperature, unless otherwise specified. In this specification, room temperature refers to a temperature in the range of 10 to 40° C.

1. Solid Composition

The solid composition of the present invention comprises
(1) an amorphous poorly water-soluble polyphenol,
(2) a hydrophilic polymer, and
(3) at least one nonionic surfactant selected from the group consisting of polyglycerol fatty acid esters, sucrose fatty acid esters, and lecithins.

(1) Polyphenol

In general, almost all polyphenols are crystalline and are thus poorly soluble in water or insoluble in water.

The polyphenol contained in the solid composition of the present invention is an "amorphous poorly water-soluble polyphenol."

The "poorly water-soluble polyphenol compound" in the present invention has a solubility in pure water of 0.1 mass % or less at 25° C., or has an octanol/water partition coefficient (log P) within the range of −1.0 to 4.0. The log P value can be determined by high-performance liquid chromatography according to JIS Z 7260-117 (2006). The log P value is defined by the following formula: log P=log (Coc/Cwa)

Coo: concentration of the test substance in the 1-octanol layer

Cwa: concentration of the test substance in the aqueous layer

The "poorly water-soluble polyphenol compound" in the present invention preferably has a solubility in the second dissolution medium of the Japanese Pharmacopoeia, 16th edition, of 0.2 mg/100 mL or less, as determined in accordance with the method prescribed in the Japanese Pharmacopoeia dissolution test.

In this specification, "polyphenol" means a compound having two or more phenolic hydroxy groups in the same molecule.

Examples of "amorphous poorly water-soluble polyphenols" contained in the solid composition of the present invention include the following. The following amorphous poorly water-soluble polyphenols mentioned as examples may be in the form of compounds or compositions.

1. phenolic acids (e.g., hydroxycinnamic acid (e.g., p-coumaric acid, caffeic acid, ferulic acid), hydroxybenzoic acid (e.g., p-hydroxybenzoic acid, gallic acid, and ellagic acid), and rosmarinic acid);
2. flavonoids (flavones (e.g., luteolin, apigenin, flavoxate, diosmin, and nobiletin), flavanones (e.g., hesperetin, naringenin, hesperidin, and hesperetin), flavanols (e.g., quercetin, myricetin, simylarin, silymarin, silybinin, rutin, and isoquercitrin), flavan-3-ol, catechin (E), epicatechin (EC), theaflavin, epicatechin gallate (ECg), epigallocatechin (EGC), epigallocatechin gallate (EGCg), isoflavones (e.g., genistein and daidzein), anthocyanidins (e.g., cyanidins, delphinidins, malvidins, pelargonidins, peonidins, proanthocyanidins, oligomeric proanthocyanidins (OPC), procyanidins, and polycyanidin;
3. stilbenoids (e.g., resveratrol);
4. tannins (e.g., condensed tannins (proanthocyanidins) and hydrolyzable tannins);
5. monophenols (e.g., hydroxytyrosol and p-tyrosol);
6. capsaicinoids (e.g., capsaicin and dihydrocapsaicin);
7. curcuminoids (e.g., curcumine (keto form and enol form); dimethoxycurcumine, bisdimethoxycurcumine), and tetrahydrocurcumine,
8. aglycones thereof and derivatives thereof (e.g., acetylated compounds, malonylated compounds, methylated compounds, and glycosides).

Preferable examples include curcumine, silvmarin, and luteolin.

The solid composition of the present invention may contain one polyphenol, or two or more polyphenols.

The polyphenol contained in the solid composition of the present invention may be, for example, in the form of an extract derived from a natural product.

Examples of such extracts include turmeric extract, blessed thistle extract, coffee extract, licorice extract, cucumber extract, *Spatholobus suberectus Dunn* extract, gentian (or *Gentiana scabra*) extract, *Geranium thunbergii* extract, cholesterol and derivatives thereof, hawthorn extract, *Paeonia lactiflora* extract, *Gingko biloba* extract, *Scutellaria baicalensis* (or *scutellaria* root) extract, carrot extract, *Rosa rugosa* (or ramanas rose, *rugosa* rose) extract, *Sanpenzu* (or *cassia*) extract, *Tormentilla* extract, parsley extract, *Paeonia suffruticosa* (or cortex moutan) extract, *Mokka* (or *Chaenomeles lagenaria* Koidz) extract, Melissa extract, *Alnus firma* fruit (or *Alnus firma*) extract, saxifrage extract, rosemary (or *Rosmarinus officinalis* L.) extract, lettuce extract, tea extract (e.g., oolong tea extract, black tea extract, green tea extract), microorganism fermentation metabolites, *Fructus momordicae* extract, and the like.

In a preferred embodiment of the present invention, the amorphous poorly water-soluble polyphenol comprises curcumin.

The amorphous poorly water-soluble polyphenol content of the solid composition of the present invention is preferably within the range of 1 to 50 mass %, more preferably 5 to 40 mass %, and even more preferably 10 to 30 mass %.

Although the solid composition of the present invention may contain one or more crystalline polyphenols, the proportion of the crystalline polyphenols relative to the entire solid composition or total polyphenols is preferably small.

The amorphous state of the polyphenol contained in the solid composition of the present invention can be confirmed by powder X-ray diffraction, differential scanning calorimetry, or like methods. The amount of amorphous polyphenols can be calculated from the peak areas by differential scanning calorimetry.

When the solid composition of the present invention contains "crystalline polyphenols," the types of polyphenols of the crystalline polyphenols and those of the "amorphous poorly water-soluble polyphenols" contained as an essential component in the solid composition of the present invention may be the same or different, and some of the polyphenols may be of the same type or different.

It is particularly preferable that the solid composition of the present invention is substantially or entirely free of crystalline polyphenols.

The amount of total polyphenols in the solid composition of the present invention (the "total polyphenols" include amorphous poorly water-soluble polyphenols and crystalline polyphenols) is preferably 1 to 50 mass %, more preferably 5 to 40 mass %, and even more preferably 10 to 30 mass %.

(2) Hydrophilic Polymer

The hydrophilic polymer used in the present invention is not necessarily hydrophilic or water-soluble under every conditions. The hydrophilic polymer is preferably hydrophilic or water-soluble at least at the pH in the intestinal tract.

The hydrophilic polymer used in the present invention is preferably a solid at room temperature.

The hydrophilic polymer used in the present invention preferably has a glass transition temperature (Tg) of preferably about 50° C. or more, more preferably about 80° C. to about 180° C. The determination of the glass transition temperature (Tg) can be performed according to JIS K 7121: 2012.

The solid composition of the present invention may contain one hydrophilic polymer, or two or more hydrophilic polymers.

Examples of the hydrophilic polymer used in the present specification include the following.

(1) homopolymers of N-vinyllactam (preferably N-vinylpyrrolidone) (e.g., polyvinylpyrrolidones (i.e., PVP or povidone) (e.g., Kollidon™ 12PF, Kollidon™ 17PF, Kollidon™ 25, Kollidon™ 30, Kollidon™ 90F, or equivalents thereof), and copolymers thereof (e.g., a copolymer of N-vinylpyrrolidone and vinyl acetate monomers (i.e., copovidone), or a copolymer of N-vinylpyrrolidone and vinyl propionate monomers);

(2) cellulose esters and cellulose ethers, in particular, methyl cellulose, ethyl cellulose, hydroxyalkyl cellulose (e.g., hydroxypropyl cellulose (i.e., HPC)), hydroxyalkyl alkyl cellulose (e.g., hydroxypropyl methylcellulose (namely, HPMC)), or hypromellose (e.g., Methocel™ E3, Methocel™ E5, Methocel™ E6, Methocel™ E15, or equivalents thereof, Methocel™ K3, or equivalents thereof), cellulose phthalate, and cellulose succinate (e.g., cellulose acetate phthalate, hydroxypropyl methylcellulose phthalate, hydroxypropyl methylcellulose succinate, and hydroxypropyl methylcellulose acetate succinate (i.e., HPMC-AS));

(3) high-molecular-weight polyalkylene oxides (e.g., polyethylene oxide, polypropylene oxide, and ethylene oxide, and copolymers of propylene oxide (e.g., poloxamers));

(4) polyacrylate and polymethacrylate (e.g., methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), and poly(hydroxyalkyl methacrylate));

(5) polyacrylamides;

(6) vinyl acetate copolymers and copolymers of polyvinyl alcohol; oligosaccharide and polysaccharides (e.g., carrageenan, galactomannan, and xanthan gum);

and mixtures of two or more of the above compounds.

In one preferable embodiment of the present invention, the solid composition of the present invention contains as the hydrophilic polymer at least one member selected from the group consisting of polyvinylpyrrolidone, hydroxypropyl cellulose, and hydroxypropyl methylcellulose, and may further contain other hydrophilic polymers.

In one particularly preferable embodiment of the present invention, the solid composition of the present invention contains at least a polyvinylpyrrolidone as the hydrophilic polymer and may further contain other hydrophilic polymers.

In another preferable embodiment of the present invention, the hydrophilic polymer is at least one member selected from the group consisting of polyvinylpyrrolidone, hydroxypropyl cellulose, and hydroxypropyl methylcellulose.

In another particularly preferable embodiment, the hydrophilic polymer is polyvinylpyrrolidone.

The hydrophilic polymer content of the solid composition of the present invention is preferably in the range of 5 to 90 mass %, more preferably 20 to 90 mass %, and even more preferably 40 to 90 mass %.

(3) Nonionic Surfactant

The nonionic surfactant contained in the solid composition of the present invention is a nonionic surfactant that is at least one member selected from the group consisting of polyglycerol fatty acid esters, sucrose fatty acid esters, and lecithins.

Examples of polyglycerol fatty acid esters used in the present invention include esters of (a) polyglycerols having an average degree of polymerization of 2 or more, (preferably 3 to 15, more preferably 3 to 10) and (b) fatty acids having 8 to 18 carbon atoms (e.g., caprylic acid, capric acid, lauric acid, myristic acid, palmitic acid, stearic acid, oleic acid, and linoleic acid).

Specific examples of polyglycerol fatty acid esters used in the present invention include diglycerol monolaurate, diglycerol monostearate, diglycerol monooleate, decaglycerol monolaurate, decaglycerol monostearate, and decaglycerol monooleate.

In the present invention, the polyglycerol fatty acid esters can be used singly or in a combination of two more.

The HLB value of sucrose fatty acid esters used in the present invention preferably has an HLB value of 10 or more, and preferably 12 or more.

The fatty acid of the sucrose fatty acid ester used in the present invention preferably has at least 12 carbon atoms, and more preferably 12 to 20 carbon atoms.

Specific examples of sucrose fatty acid esters preferably used in the present invention include sucrose laurate, sucrose myristate, sucrose palmitate, sucrose stearate, sucrose oleate, sucrose behenate, and sucrose erucate.

In the present invention, the sucrose fatty acid esters can be used singly or in a combination of two or more.

The lecithin used in the present invention is an adduct of a phosphoric acid derivative of di-fatty acid ester of glycerol (diglyceride). Lechithin is widely distributed in plant and animal bodies.

Examples of the lecithin used in the present invention include egg yolk lecithin contained in egg yolk, soybean lecithin contained in soybeans, and sunflower lecithin contained in sunflowers.

Examples of the lecithin used in the present invention include fractionated lecithin obtained by extracting an active ingredient from a lecithin described above, enzymatically modified lecithin obtained by treating lecithin with an enzyme, and enzymatically decomposed lecithin.

Specific examples of the lecithin used in the present invention include lecithin, enzymatically decomposed lecithin (phosphatidic acid), lysolecithin, soybean lecithin (soybean phospholipid), and egg yolk lecithin.

Lecithins that can be used in the present invention are commercially available. For example, SLP-White (trade name, produced by Tsuji Oil Mill Co., Ltd.) can be used. In the present invention, lecithins can be used singly, or in a combination of two or more.

Particularly suitable examples of the nonionic surfactant contained in the solid composition of the present invention include polyglycerol fatty acid esters.

The solid composition of the present invention may contain one or more nonionic surfactants.

In a preferred embodiment of the present invention, the nonionic surfactant is a polyglycerol fatty acid ester.

The nonionic surfactant content of the solid composition of the present invention is preferably in the range of 5 to 90 mass %, more preferably 5 to 60 mass %, and even more preferably 10 to 40 mass %.

(4) Other Components

If desired, the solid composition of the present invention may contain components other than those mentioned above, as long as the effect of the present invention is not impaired.

Examples of such components include excipients, fillers, extenders, binders, disintegrators, surfactants, seasonings, flavoring agents, and lubricants.

As long as the effect of the present invention is not impaired, the types and amounts of such components may be suitably selected and designed based on common general technical knowledge.

2. Use and Form of the Solid Composition

The composition of the present invention can be used for foods, functional foods, dietary supplement foods (supplements), food for specified health uses (FOSHU), quasi-drugs, medicine, etc.

The solid composition of the present invention is preferably an oral preparation.

The oral preparation is preferably in the form of, for example, tablets, granules, powders, fine granules, granules, pills, or troches. The composition of the present invention can be used as a material for producing such a preparation.

In this case, the amount of the solid composition (oral polyphenol preparation) of the present invention administered or ingested may vary according to the type of polyphenol, age, body weight, and condition of the user, form of administration, and treatment period. For example, when the polyphenol is curcumin, the WHO Technical Report series shows that the ADI of curcumine is 0 to 3 mg/kg body weight/day and that the NOAEL of curcumine is 250 to 320 mg/kg body weight/day (WHO Technical Report Series: 1237259778265_0.pdf, page 33). The polyphenol in an amount within this range can be preferably administered or ingested once a day, or in divided doses several times a day (e.g., twice, three times, four times, or five times).

The solid composition obtained by the present invention can be used not only for foods or the like but also can be used by incorporation into, for example, cosmetics.

Examples of the form of such cosmetics include skin care cosmetics such as lotions, creams, face lotions, emulsions, and serums; hair care products, such as shampoos; mouthwashes; and the like. Further, any components that are commonly used in the field of cosmetics can be used in combination.

Examples of surfactants include anionic surfactants such as glycerol fatty acid esters, propylene glycol fatty acid esters, sorbitan fatty acid esters, polyoxyethylene alkyl ethers, polyoxyethylene alkyl phenyl ethers, polyoxyethylene fatty acid esters, carboxylic acid salts, and sulfonic acid salts; and cationic surfactants such as amine salts and ammonium salts. For example, at least one of such surfactants can be used in combination with the solid composition of the present invention.

When orally administered or ingested, the solid composition of the present invention exhibits a high ability to dissolve a polyphenol into the body fluid (preferably intestinal fluid) for a prolonged period of time, thus enabling efficient ingestion of the polyphenol.

3. Method for Producing the Solid Composition

The composition of the present invention can be produced, for example, by a production method comprising the step of mixing (1) a crystalline polyphenol,
(2) a hydrophilic polymer, and
(3) at least one nonionic surfactant selected from the group consisting of polyglycerol fatty acid esters, sucrose fatty acid esters, and lecithins,
optionally with (4) other components,
the method comprising the step of converting the crystalline polyphenol to an amorphous polyphenol.

In the mixing step, the above components can be mixed simultaneously or successively.

The mixing step can be preferably performed without using a solvent such as an organic solvent.

Even when the solvent is used, the above components, such as a polyphenol, do not have to be completely dissolved in the solvent.

This allows the composition of the present invention to be produced at low cost without using a large container or the like.

The step of mixing the components and the step of converting the crystalline polyphenol to an amorphous polyphenol can be separate steps, or they can be partially or completely in common.

A higher conversion of crystalline polyphenol to amorphous polyphenols is preferable. Converting all or substantially all the crystalline polyphenol to amorphous polyphenols is particularly preferable.

The composition of the present invention can be produced, for example, by solvent precipitation methods, spray-drying methods, freeze-drying methods, vacuum-drying methods, or kneading methods, or a combination of these methods.

The composition of the present invention is preferably produced by a production method comprising the step of kneading (1) an amorphous poorly water-soluble polyphenol,
(2) a hydrophilic polymer, and
(3) at least one nonionic surfactant selected from the group consisting of polyglycerol fatty acid esters, sucrose fatty acid esters, and lecithins,
optionally with (4) other components.

In the kneading step, the crystalline polyphenol, the hydrophilic polymer, and the nonionic surfactant are preferably kneaded simultaneously. The kneading converts a part of the crystalline polyphenol to amorphous polyphenol, or preferably converts all or substantially all the crystalline polyphenol to amorphous polyphenol.

The kneading can be preferably performed, for example, by using a single-screw extruder, an intermeshing screw extruder, or a multi-screw extruder (e.g., a twin-screw extruder). The kneading can also be preferably performed by kneading with a relatively weak force, such as kneading by hand using a spatula or the like on a hot plate.

In this kneading, for example, the mixture is heated to the temperature at which the components are dissolved, and kneaded. After the components are dissolved, the solution is cooled to room temperature. The obtained solid composition is pulverized into a powder using a pulverizer to obtain a composition of the present invention.

The composition of the present invention can preferably have a primary particle diameter of, for example, 0.1 to 500 μm.

The composition of the present invention can be preferably produced, for example, by a method comprising the steps of: fully mixing the crystalline polyphenol, the hydrophilic polymer, and the nonionic surfactant with an oil or fat to prepare a slurry in which the polyphenol is dissolved; and drying the slurry.

Examples of drying methods include spray-drying methods, freeze-drying methods, vacuum-drying methods, drum-drying methods, far-infrared drying methods, and the like. Spray-drying methods are particularly preferable.

EXAMPLES

The present invention is described below in more detail with reference to Examples. However, the scope of the present invention is not limited to these Examples.

In the Examples below, symbols and abbreviations have the following meanings:
CUR: Curcumin
SIL: Silvmarin
LUT: Luteolin
PVP: Polyvinylpyrrolidones
PGFE: Polyglycerol fatty acid ester
HPC: Hydroxypropyl cellulose
HPMC: Hydroxypropyl methylcellulose
Method for Preparing Samples The compositions having formulations shown below in Tables 1-1, 1-2, or 1-3 were each heated to the melting temperature and kneaded. After melting, the compositions were cooled to room temperature and formed into powders using a pulverizer. The powders thus obtained were used.

In the preparation of the composition of Comparative Example 3, however, the components were merely mixed without heating, and the resulting composition was used as a sample.

The heat kneading was performed by setting a hot plate at 240° C. for curcumine and silymarin, and at 350° C. for luteolin, and each composition was then kneaded by hand using a spatula or the like until it was melted.

The components used in the Examples or Comparative Examples are described below. Except for PGFE(A), commercially available products were purchased and used. PGFE(A) is a polyglycerol myristic acid ester of HLB12.
Components
Curcumin
  Curcumine material (purity: curcumine 90% or more) (bulk curcumine powder)
Hydrophilic Polymer
  Koridon K30 (trade name, BASF A.G.): PVP (polyvinylpyrrolidones)
Nonionic Surfactants
PGFE(A):
  PGFE (polyglycerol fatty acid ester)
Ryoto polyglyester 1-50SV (trade name, produced by Mitsubishi-Chemical Foods Corporation):
  PGFE (decaglycerin stearic acid ester)
Ryoto polyglyester M-10D (trade name, Mitsubishi-Chemical Foods Corporation):
  PGFE (decaglycerol myristic acid ester)
NIKKOL HCO-60 (trade name, Nikko Chemicals Co., Ltd.): polyoxyethylene hydrogenated castor oil
NIKKOL TS-10V (trade name, Nikko Chemicals Co., Ltd.): polyoxyethylene sorbitan higher fatty acid ester (Polysorbate 60)
NIKKOL TO-10V (trade name, Nikko Chemicals Co., Ltd.): polyoxyethylene sorbitan higher fatty acid ester (Polysorbate 80)
NIKKOL TMGS-15V (trade name, Nikko Chemicals Co., Ltd.): polyoxyethylene glyceryl monostearate

TABLE 1-1

|  | Curcumine material (wt %) | Hydrophilic polymer | | Nonionic surfactant | | Total |
| --- | --- | --- | --- | --- | --- | --- |
|  |  | Type | (wt %) | Type | (wt %) |  |
| Example 1 | 11 | Koridon K30 | 64 | PGFE (A) | 25 | 100 |
| Example 2 | 11 | Koridon K30 | 64 | Ryoto Polyglyester M-10D | 25 | 100 |
| Example 3 | 11 | Koridon K30 | 64 | Ryoto Polyglyester 1-50SV | 25 | 100 |
| Example 4 | 14 | Koridon K30 | 76 | PGFE (A) | 10 | 100 |
| Example 5 | 7.5 | Koridon K30 | 42.5 | PGFE (A) | 50 | 100 |
| Example 6 | 11 | Koridon K30 | 64 | Ryoto sugar ester P-1560 | 25 | 100 |
| Example 7 | 11 | Koridon K30 | 64 | Ryoto sugar ester P-1670 | 25 | 100 |
| Example 8 | 11 | Koridon K30 | 64 | SLP white | 25 | 100 |
| Example 9 | 11 | Koridon K30 | 64 | Solec K-EML | 25 | 100 |

TABLE 1-1-continued

| | Curcumine material (wt %) | Hydrophilic polymer Type | (wt %) | Nonionic surfactant Type | (wt %) | Total |
|---|---|---|---|---|---|---|
| Comparative Example 1 | 15 | Koridon K30 | 85 | — | — | 100 |
| Comparative Example 2 | 30 | — | 0 | PGFE (A) | 70 | 100 |
| Comparative Example 3 | 11 | Koridon K30 | 64 | PGFE (A) | 25 | 100 |
| Comparative Example 4 | 11 | Koridon K30 | 64 | NIKKOL HCO-60 | 25 | 100 |
| Comparative Example 5 | 11 | Koridon K30 | 64 | NIKKOL TO-10V | 25 | 100 |
| Comparative Example 6 | 11 | Koridon K30 | 64 | NIKKOL TO-10V | 25 | 100 |
| Comparative Example 7 | 11 | Koridon K30 | 64 | NIKKOL TMGS-15V | 25 | 100 |

TABLE 1-2

| Sample | Silymarin material (wt %) | Hydrophilic polymer Type | (wt %) | Nonionic surfactant Type | (wt %) | Total |
|---|---|---|---|---|---|---|
| Example 10 | 11 | Koridon K30 | 64 | PGFE (A) | 25 | 100 |
| Comparative Example 8 | 15 | Koridon K30 | 85 | — | 0 | 100 |
| Comparative Example 9 | 30 | — | 0 | PGFE (A) | 70 | 100 |

TABLE 1-3

| Sample | Luteolin material (wt %) | Hydrophilic polymer Type | (wt %) | Nonionic surfactant Type | (wt %) | Total |
|---|---|---|---|---|---|---|
| Example 11 | 11 | Koridon K30 | 64 | PGFE (A) | 25 | 100 |
| Comparative Example 10 | 15 | Koridon K30 | 85 | — | 0 | 100 |
| Comparative Example 11 | 30 | — | 0 | PGFE (A) | 70 | 100 |

The compositions obtained in Examples 1 to 9, Comparative Example 1, and Comparative Examples 4 to 7 were subjected to powder X-ray diffraction measurement. The results show that peaks of crystalline curcumine were completely or Partially lost, and the compositions were confirmed to contain amorphous curcumine. The composition obtained in Comparative Example 2 was subjected to differential scanning calorimetry. The results show that peaks of crystalline curcumine decreased, and the composition was confirmed to contain amorphous curcumine. Since the composition was obtained by merely mixing the components in Comparative Example 3, the composition is naturally assumed to contain crystalline curcumin.

Dissolution Test Method

The dissolution test was performed by using the following materials and conditions in accordance with the test method prescribed in the Japanese Pharmacopoeia, 16th edition. The analysis was performed by sampling a small amount of the test fluid at each time.

Materials and Conditions of the Dissolution Test
[1] Curcumin Dissolution Test
Dissolution tester: PJ-32S (product name, produced by Miyamoto Riken Ind. Co., Ltd.)
Test fluid: second dissolution medium of the Japanese Pharmacopoeia (stimulated intestinal fluid, pH 6.8)
Test sample amount: 10 mg/100 ml in terms of curcumin
Temperature: 37° C.
Sampling: after filtration through a 0.2-μm membrane, the filtrate was analyzed.
Analysis: the HPLC method

[2] Silymarin Dissolution Test
Dissolution tester: PJ-32S (product name, produced by Miyamoto Riken Ind. Co., Ltd.)
Test fluid: second dissolution medium of the Japanese Pharmacopoeia (simulated intestinal fluid, pH 6.8)
Sample amount: 10 mg/100 ml in terms of silymarin
Temperature: 37° C.
Sampling: after filtration through a 0.2-μm membrane filter, the filtrate was analyzed.
Analysis: the HPLC method

[3] Luteolin Dissolution Test
Dissolution tester: PJ-32S (product name, produced by Miyamoto Riken Ind. Co., Ltd.)
Test fluid: second dissolution medium of the Japanese Pharmacopoeia (stimulated intestinal fluid, pH 6.8)
Test sample amount: 10 mg/100 ml in terms of luteolin
Temperature: 37° C.
Sampling: After filtration through a 0.2-μm membrane filter, the filtrate was analyzed.
Analysis: the HPLC method The test results are shown below.

Test Example 1-1

Figure 11:
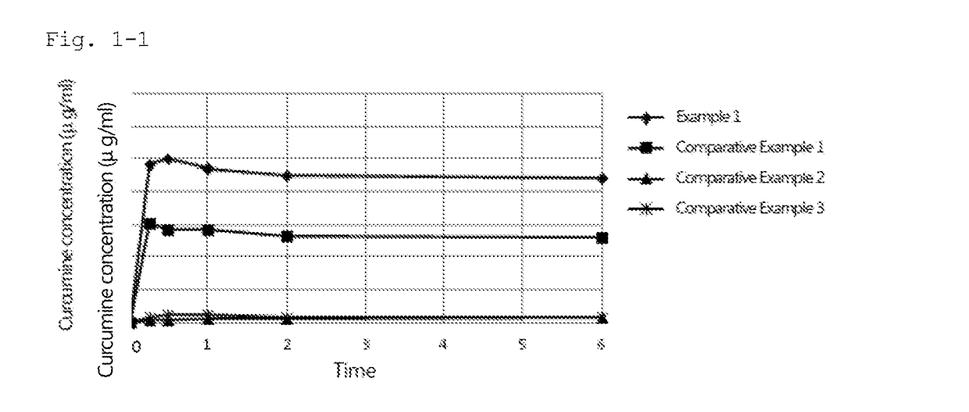

Using the samples shown in Table 2-1, changes in dissolution of curcumine in simulated intestinal fluid over time from the composition of the present invention in comparison with those from a solid composition not containing a surfactant, a solubilized preparation, and a solid composition prepared without heating were tested. Table 3-1 and FIG. 1-1 show the results. As can be understood from these results, the composition of the present invention exhibited a high ability to dissolve the polyphenol into the body fluid (preferably intestinal fluid) for a prolonged period of time.

Test Example 1-2

Figure 12:
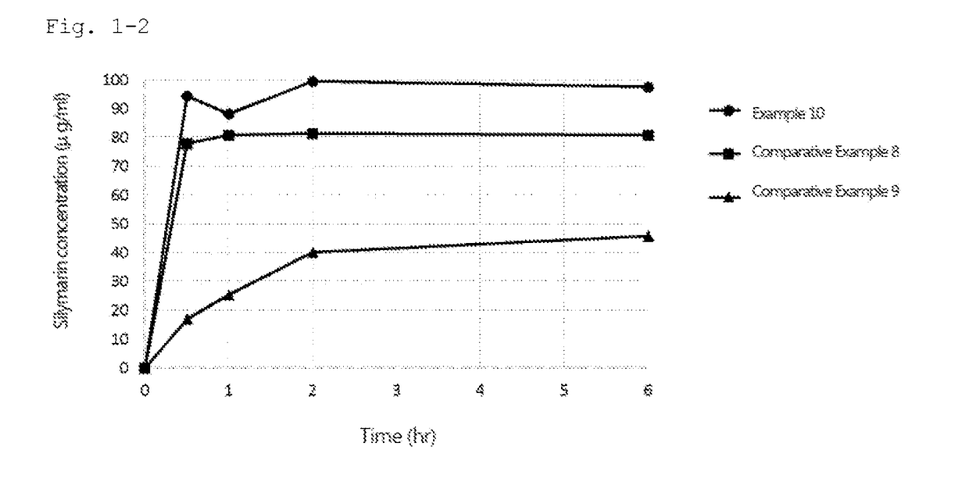

Using the samples shown in Table 2-2, changes in dissolution of silymarin in simulated intestinal fluid over time from the composition of the present invention in comparison with those from a solid composition not containing a surfactant and a solubilized preparation were tested. Table 3-2 and FIG. 1-2 show the results. As can be understood from these results, the composition of the present invention exhibited a high ability to dissolve the polyphenol into the body fluid (preferably intestinal fluid) for a prolonged period of time.

Test Example 1-3

Figure 13:
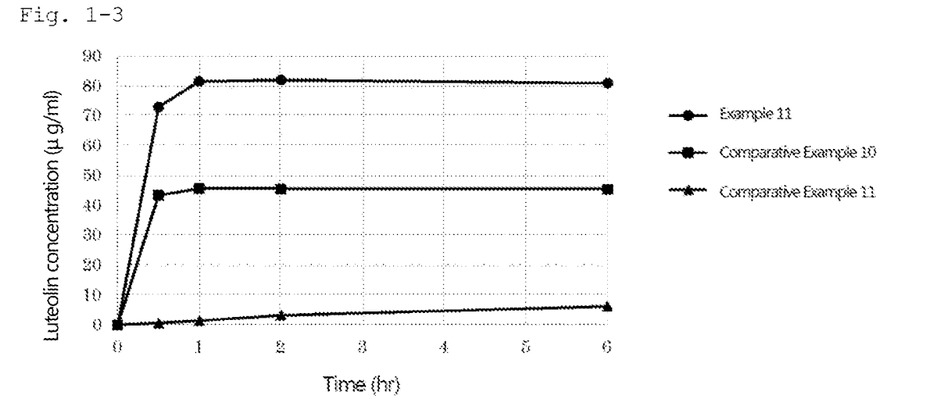

Using the samples shown in Table 2-3, changes in dissolution of luteolin in simulated intestinal fluid over time from the composition of the present invention in comparison with those from a solid composition not containing a surfactant and a solubilized preparation were tested. Table 3-3 and FIG. 1-3 show the results. As can be understood from these results, the composition of the present invention exhibited a high ability to dissolve the polyphenol into the body fluid (preferably intestinal fluid) for a prolonged period of time.

TABLE 3-1

| Sample | Curcumine concentration at each time (hr) (μg/ml) | | | | | |
|---|---|---|---|---|---|---|
|  | 0 hr | 0.25 hr | 0.5 hr | 1 hr | 2 hr | 6 hr |
| Example 1 | 0 | 48.1 | 49.9 | 47.0 | 44.9 | 44.2 |
| Comparative Example 1 | 0 | 30.4 | 28.3 | 28.6 | 26.3 | 25.8 |
| Comparative Example 2 | 0 | 0.8 | 0.9 | 1.0 | 1.2 | 1.6 |
| Comparative Example 3 | 0 | 1.7 | 2.3 | 2.3 | 1.7 | 1.5 |

TABLE 2-1

| Sample | Formulation (Numerical values are in wt %.) | Curcumine material:PVP (Numerical values are mass ratios.) | Curcumine material:PGFE (Numerical values are mass ratios.) | Remarks |
|---|---|---|---|---|
| Example 1 | Curcumine material:11/PVP:64/PGFE(A):25 | 15:85 | 30:70 | Amorphous preparation (containing PGFE) |
| Comparative Example 1 | Curcumine material:15/PVP:85 | 15:85 | — | Amorphous preparation (not containing PGFE) |
| Comparative Example 2 | Curcumine material:30/PGFE(A):70 | — | 30:70 | Solubilized preparation |
| Comparative Example 3 | Curcumine material:11/PVP:64/PGFE(A):25 | 15:85 | 30:70 | The same formulation as in Example 1 but produced without heating |

TABLE 2-2

| Sample | Formulation (Numerical values are in wt %.) | Silymarin material:PVP (Numerical values are mass ratios.) | Silymarin material:PGFE (Numerical values are mass ratios.) | Remarks |
|---|---|---|---|---|
| Example 10 | Silymarin material:11/PVP:64/PGFE(A):25 | 15:85 | 30:70 | Amorphous preparation (containing PGFE) |
| Comparative Example 8 | Silymarin material:15/PVP:85 | 15:85 | — | Amorphous preparation (not containing PGFE) |
| Comparative Example 9 | Silymarin material:30/PGFE (A):7G | — | 30:70 | Solubilized preparation |

TABLE 2-3

| Sample | Formulation (Numerical values are in wt %.) | Luteolin material:PVP (Numerical values are mass ratios.) | Luteolin material:PGFE (Numerical values are mass ratios.) | Remarks |
|---|---|---|---|---|
| Exarriple 11 | Luteolin material:11/PVP:64/PGFE(A):25 | 15:85 | 30:70 | Amorphous preparation (containing PGFE) |
| Comparative Example 10 | Luteolin material:15/PVP:85 | 15:85 | — | Amorphous preparation (not containing PGFE) |
| Comparative Example 11 | Luteolin material:30/PGFE(A):70 | — | 30:70 | Solubilized preparation |

TABLE 3-2

| Sample | Silymarin concentration at each time (hr) (μg/ml) | | | | |
|---|---|---|---|---|---|
| | 0 hr | 0.5 hr | 1 hr | 2 hr | 6 hr |
| Example 10 | 0 | 94.5 | 88.3 | 99.6 | 97.6 |
| Comparative Example 8 | 0 | 78.0 | 80.9 | 81.5 | 80.9 |
| Comparative Example 9 | 0 | 16.9 | 25.4 | 40.2 | 45.8 |

TABLE 3-3

| Sample | Luteolin concentration at each time (hr) (μg/ml) | | | | |
|---|---|---|---|---|---|
| | 0 hr | 0.5 hr | 1 hr | 2 hr | 6 hr |
| Example 11 | 0 | 72.9 | 81.6 | 82.0 | 80.9 |
| Comparative Example 10 | 0 | 43.4 | 45.6 | 45.5 | 45.4 |
| Comparative Example 11 | 0 | 0.6 | 1.4 | 3.2 | 6.2 |

Test Example 2

Figure 2:
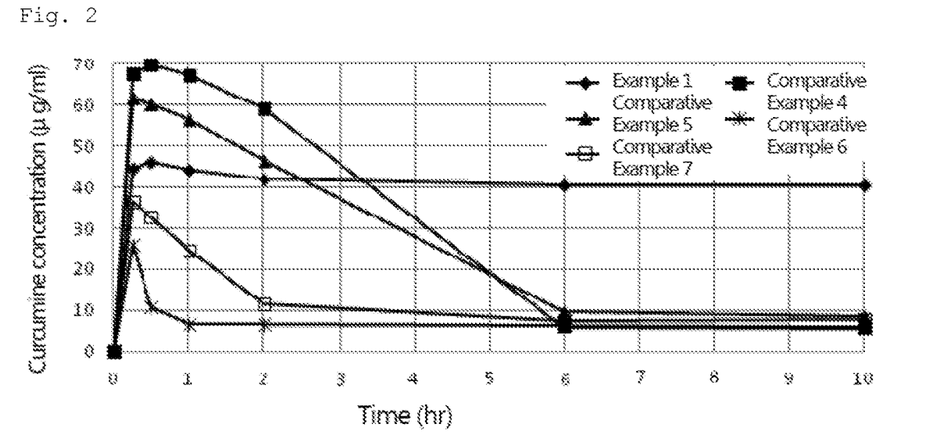
FIG. 2 is a graph showing changes in dissolution of curcumine into simulated intestinal fluid over time from the preparation obtained in Example 1, in comparison with those from the preparations containing various nonionic surfactants other than the nonionic surfactant used in the present invention (Comparative Examples 4 to 7).

Using the samples shown in Table 4, changes in dissolution of curcumine into simulated intestinal fluid over time from the composition of the present invention comprising a specific surfactant, in comparison with those from the corresponding compositions comprising other nonionic surfactants, were tested. Table 5 and FIG. 2 show the results. As can be understood from these results, only when the composition of the present invention contained a specific nonionic surfactant did the composition of the present invention exhibit a high ability to dissolve the polyphenol into the body fluid (preferably intestinal fluid) for a prolonged period of time.

TABLE 4

| Sample | Formulation (Numerical values are in wt %.) | Curcumine material:PVP (Numerical values are mass ratios. | Curcumine material:Nonionic surfactant (Numerical values are mass ratios.) | Remarks |
|---|---|---|---|---|
| Example 1 | Curcumine material:11/PVP:64/FGFE(A):25 | 15:85 | 30:70 | PGFE |
| Comparative Example 4 | Curcumine material:11/PVP:64/HCO60:25 | 15:85 | 30:70 | Polyoxyethylene hydrogenated castor oil |
| Comparative Example 5 | Curcumine material:11/PVP:64/TS10V:25 | 15:85 | 30:70 | Polysorbate 60 |
| Comparative Example 6 | Curcumine material:11/PVP:64/TO10V:25 | 15:85 | 30:70 | Polysorbate 80 |
| Comparative Example 7 | Curcumine material:11/PVP:64/TMGS15V:25 | 15:85 | 30:70 | Polyoxyethylene glyceryl monostearate |

TABLE 5

| Sample | Curcumine concentration at each time (hr) (μg/ml) | | | | | | |
|---|---|---|---|---|---|---|---|
| | 0 hr | 0.25 hr | 0.5 hr | 1 hr | 2 hr | 6 hr | 10 hr |
| Example 1 | 0 | 44.7 | 46.3 | 44.5 | 42.1 | 40.6 | 40.7 |
| Comparative Example 4 | 0 | 67.5 | 70.0 | 67.5 | 59.0 | 6.1 | 5.4 |
| Comparative Example 5 | 0 | 61.9 | 60.4 | 56.4 | 46.7 | 9.6 | 8.7 |
| Comparative Example 6 | 0 | 25.9 | 10.8 | 6.8 | 6.6 | 6.3 | 5.9 |
| Comparative Example 7 | 0 | 36.5 | 32.8 | 24.8 | 11.6 | 7.5 | 7.8 |

Test Example 3

Figure 3:
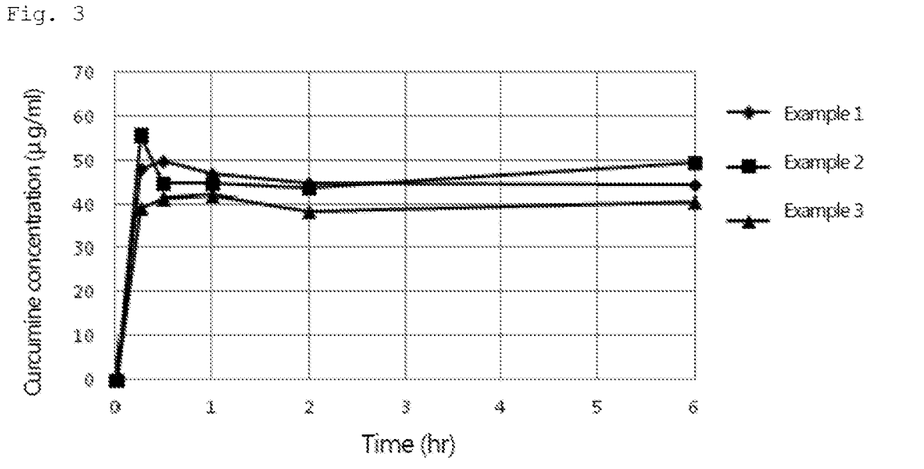
FIG. 3 is a graph showing changes in dissolution of curcumine into simulated intestinal fluid over time from curcumine-containing preparations produced by using various polyglycerol fatty acid esters (Examples 1 to 3).

Using the samples shown in Table 6 in which various types of polyglycerol fatty acid esters were used, chances in dissolution of curcumine into simulated intestinal fluid over time were tested. Table 7 and FIG. 3 show the results. As can be understood from this, the compositions of the present invention containing various types of polyglycerol fatty acid esters exhibited a high ability to dissolve the polyphenol into the body fluid (preferably intestinal fluid) for a prolonged period of time.

TABLE 6

| Sample | Formulation (Numerical values are in wt %.) | Curcumine material:PVP (Numerical values are mass ratios.) | Curcumine material:PGFE (Numerical values are mass ratios.) | Remarks |
|---|---|---|---|---|
| Example 1 | Curcumine material:11/PVP:64/PGFE(A):25 | 15:85 | 30:70 | PGFE(A) |
| Example 2 | Curcumine material:11/PVP:64/M-10D:25 | 15:85 | 30:70 | PGFE M-10D |
| Example 3 | Curcumine material:11/PVP:64/1-50SV:25 | 15:85 | 30:70 | PGFE 1-50SV |

TABLE 7

| | Curcumine concentration at each time (hr) (μg/ml) | | | | | |
|---|---|---|---|---|---|---|
| Sample | 0 hr | 0.25 hr | 0.5 hr | 1 hr | 2 hr | 6 hr |
| Example 1 | 0 | 48.1 | 49.9 | 47.0 | 44.9 | 44.2 |
| Example 2 | 0 | 55.9 | 44.9 | 44.8 | 43.8 | 49.5 |
| Example 3 | 0 | 39.1 | 41.4 | 42.3 | 38.3 | 40.6 |

Test Example 4

Figure 4:
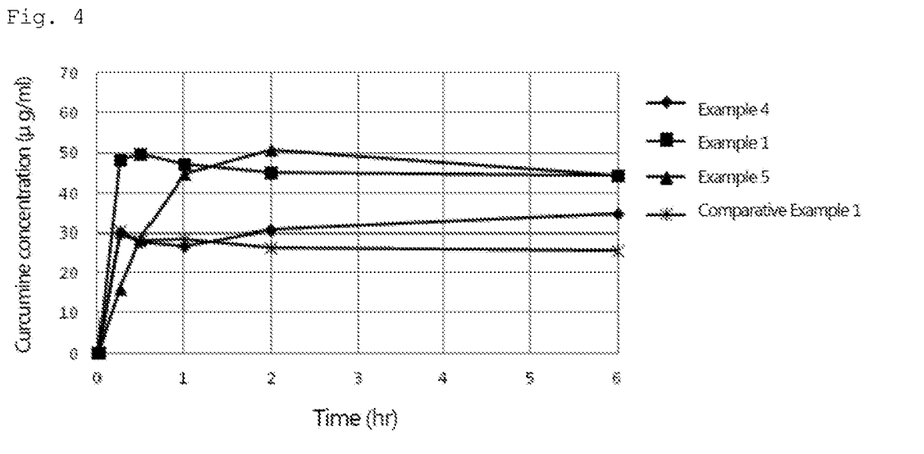
FIG. 4 is a graph showing changes in dissolution of curcumine into simulated intestinal fluid over time from curcumine-containing preparations produced by using a polyglycerol fatty acid ester in various amounts (Examples 1, 4 and 5, and Comparative Example 1).

Using the samples shown in Table 8 in which a polyglycerol fatty acid ester was used in various amounts, changes in dissolution of curcumine into stimulated intestinal fluid over time were tested. Table 9 and FIG. 4 show the results. As can be understood from these results, the compositions of the present invention containing a polyglycerol fatty acid ester in various amounts exhibited a high ability to dissolve the polyphenol into the body fluid (preferably intestinal fluid) for a prolonged period of time.

Test Example 5

Figure 5:
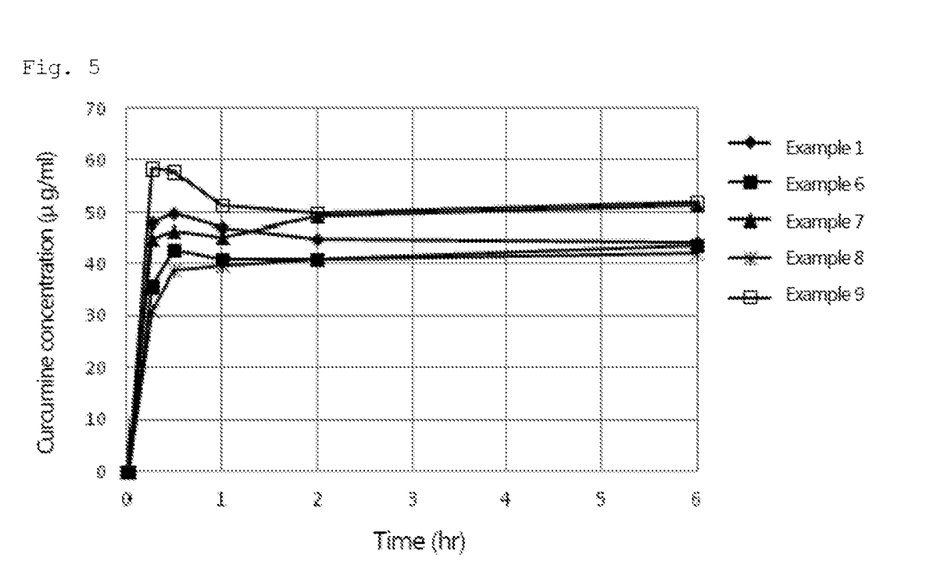
FIG. 5 is a graph showing changes in dissolution of curcumine into simulated intestinal fluid over time from curcumine-containing preparations produced by using various nonionic surfactants (Examples 1 and 6 to 9).

Using the samples shown in Table 10, changes in dissolution of curcumine into simulated intestinal fluid over time from the compositions comprising a sugar ester or a lecithin, in comparison with those of the composition comprising a polyglycerol fatty acid ester, were tested. Table 11 and FIG. 5 show the results. As can be understood from these results, the compositions of the present invention comprising a sugar ester or lecithin also exhibited a high ability to dissolve a polyphenol into the body fluid (preferably intestinal fluid) for a prolonged period of time, just like the composition comprising a polyglycerol fatty acid ester.

TABLE 8

| Sample | Formulation (Numerical values are in wt %.) | Curcumine material:PVP (Numerical values are mass ratios.) | Curcumine material:PGFE (Numerical values are mass ratios.) | Remarks |
|---|---|---|---|---|
| Example 1 | Curcumine material:11/PVP:64/PGFE(A):25 | 15:85 | 30:70 | |
| Example 4 | Curcumine material:14/PVP:76/PGFE(A):10 | 15:85 | 58:42 | The amount of PGFE used together was different. |
| Example 5 | Curcumine material:7.5/PVP:42.5/PGFE(A):50 | 15:85 | 13:87 | The amount of PGFE used together was different. |
| Comparative Example 1 | Curcumine material:15/PVP:85 | 15:85 | 100:0 | Not containing PGFE |

TABLE 9

| | Time (hr) and curcumine concentration (μg/ml) | | | | | |
|---|---|---|---|---|---|---|
| Sample | 0 hr | 0.25 hr | 0.5 hr | 1 hr | 2 hr | 6 hr |
| Example 4 | 0 | 30.0 | 27.7 | 26.9 | 30.6 | 34.7 |
| Example 1 | 0 | 48.1 | 49.9 | 47.0 | 44.9 | 44.2 |
| Example 5 | 0 | 16.2 | 28.4 | 44.6 | 50.7 | 44.1 |
| Comparative Example 1 | 0 | 30.4 | 28.3 | 28.6 | 26.3 | 25.8 |

TABLE 10

| Sample | Formulation (Numerical values are in wt %.) | Curcumine material:PVP (Numerical values are mass ratios.) | Curcumine material:Nonionic surfactant (Numerical values are mass ratios.) | Remarks |
|---|---|---|---|---|
| Example 1 | Curcumine material:11/ PVP:64/PGFE(A):25 | 15:85 | 30:70 | |
| Example 6 | Curcumine material:11/ PVP:64/P-1560:25 | 15:85 | 30:70 | Sucrose fatty acid ester |
| Example 7 | Curcumine material:11/ PVP:64/P-1670:25 | 15:85 | 30:70 | Sucrose fatty acid ester |
| Example 8 | Curcumine material:11/ PVP:64/SLP:25 | 15:85 | 30:70 | Soybean lecithin |
| Example 9 | Curcumine material:11/ PVP:64/K-EML:25 | 15:85 | 30:70 | Enzyme- treated soybean lecithin |

TABLE 11

| | Time (hr) and curcumine concentration (μg/ml) | | | | | |
|---|---|---|---|---|---|---|
| Sample | 0 hr | 0.25 hr | 0.5 hr | 1 hr | 2 hr | 6 hr |
| Example 1 | 0 | 48.1 | 49.9 | 47.0 | 44.9 | 44.2 |
| Example 6 | 0 | 35.7 | 42.7 | 41.0 | 40.8 | 43.7 |
| Example 7 | 0 | 44.8 | 46.5 | 45.0 | 49.3 | 51.2 |
| Example 8 | 0 | 31.1 | 38.8 | 39.6 | 41.0 | 42.0 |
| Example 9 | 0 | 58.5 | 57.7 | 51.4 | 49.9 | 51.9 |

Test Example 6

Compositions were prepared by the production method described above using HPC or HPMC in place of PVP, and subjected to the same test as described above. A comparison of the results with those obtained using PVP shows that the compositions comprising HPC or HPMC exhibited a low ability to dissolve polyphenol into the body fluid (preferably intestinal fluid), as compared with the composition comprising PVP, but a tendency similar to that of the composition comprising PVP was confirmed, and a high degree of dissolution of the polyphenol into the body fluid (preferably intestinal fluid) was maintained for a long time.

Test Example 7

The amorphous preparation obtained in Example 1 was administered to rats and the changes in blood curcumine concentration in the rats over time were investigated by the following test method. As a comparative example, bulk curcumine powder was administered.
Test Method
Animal: Three SD rats (male, 7 weeks old, fasted for at 14 to 16 hours before dosing) for each group.
Administration: 100 mg/kg (in terms of curcumine)/single oral administration (sonde method)
Blood sampling: Blood was sampled from the jugular vein immediately before the administration and 0.5, 1, 2, 4, 8, and 24 hours after the administration.
Analysis: 25 μl of plasma was subjected to enzymatic treatment with β-glucuronidase. After curcumine was extracted with acetonitrile, the solvent was evaporated to dryness. The resulting product was redilated with methanol and measured by UV detection (420 nm).

Figure 6:
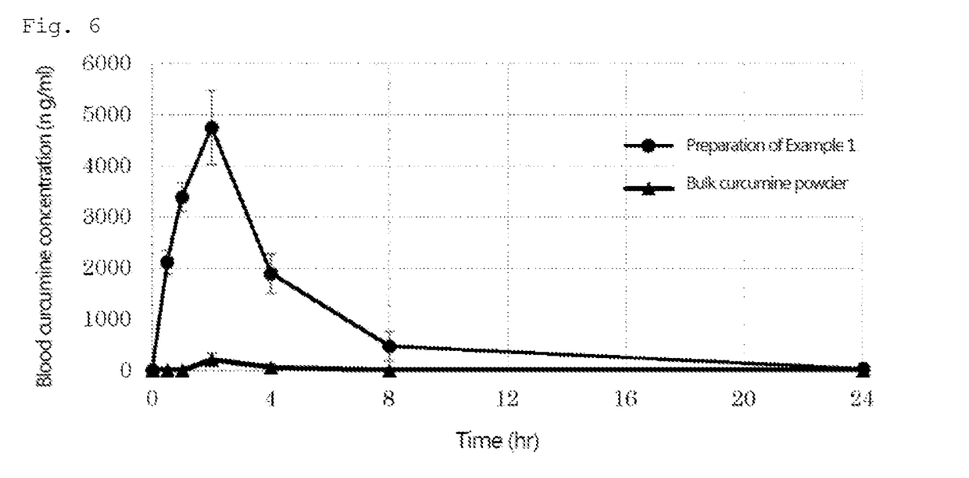
FIG. 6 is a graph showing changes in blood curcumine concentration over time in rats receiving the curcumine-containing preparation obtained in Example 1, in comparison with those in rats receiving a bulk curcumine powder as a comparative example.

FIG. 6 shows the graph of the analysis results. This confirmed that when the preparation of the present invention is used, a poorly water-soluble polyphenol can be absorbed in the living body at a high rate for a prolonged period of time.

The invention claimed is:
1. A solid composition comprising
   (1) an amorphous poorly water-soluble polyphenol,
   (2) a hydrophilic polymer, and
   (3) at least one nonionic surfactant selected from the group consisting of polyglycerol fatty acid esters and sucrose fatty acid esters.
2. The solid composition according to claim 1, wherein the amorphous poorly water-soluble polyphenol is at least one member selected from the group consisting of curcumin, silymarin, and luteolin.
3. The solid composition according to claim 1, wherein the hydrophilic polymer is at least one member selected from the group consisting of polyvinylpyrrolidone, hydroxypropyl cellulose, and hydroxypropyl methylcellulose.
4. The solid composition according to claim 1, wherein the nonionic surfactant is a polyglycerol fatty acid ester.
5. The solid composition according to claim 1, which is an oral preparation.
6. A method for producing the solid composition according to claim 1, comprising kneading the following components (1)-(3) while heating to the melting temperature of the resulting mixture comprising the components (1)-(3):
   (1) a crystalline polyphenol,
   (2) a hydrophilic polymer, and
   (3) at least one nonionic surfactant selected from the group consisting of polyglycerol fatty acid esters and sucrose fatty acid esters.
7. The method according to claim 6, wherein the crystalline polyphenol is at least one member selected from the group consisting of curcumin, silymarin, and luteolin.
8. The method according to claim 6, wherein the hydrophilic polymer is at least one member selected from the group consisting of polyvinylpyrrolidone, hydroxypropyl cellulose, and hydroxypropyl methylcellulose.
9. The method according to claim 6, wherein the nonionic surfactant is a polyglycerol fatty acid ester.
10. The method according to claim 6, which wherein the solid composition is an oral preparation.

* * * * *